Figure 1:
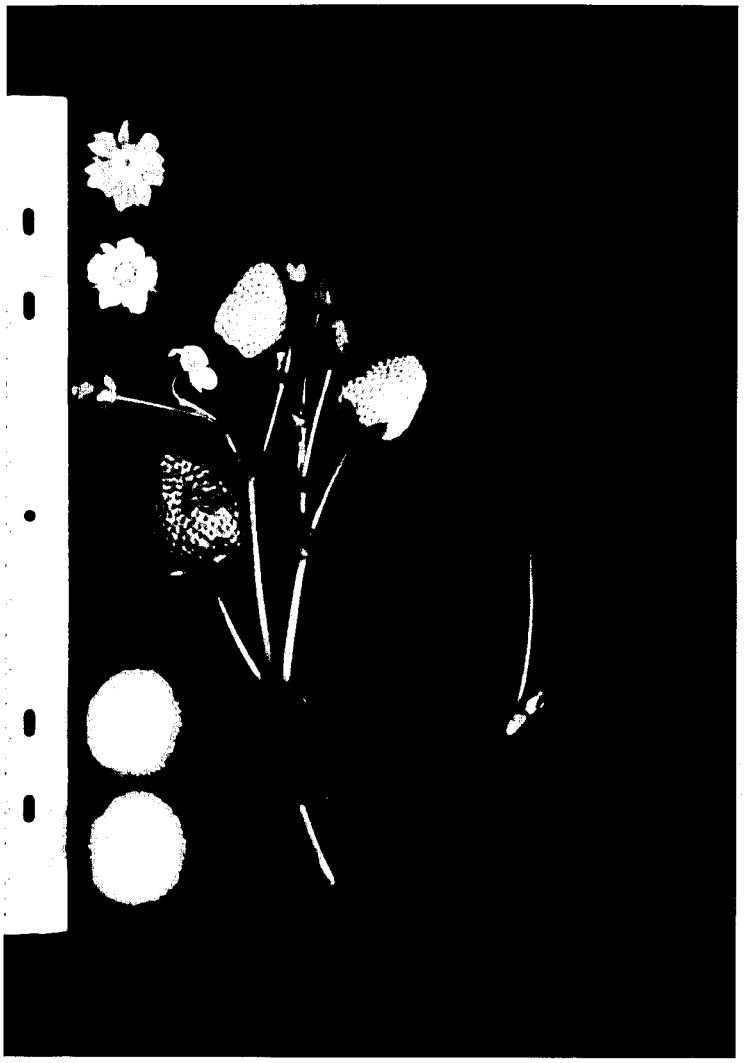

United States Patent [19]

Johnson, Jr. et al.

[11] Patent Number: Plant 7,522

[45] Date of Patent: May 14, 1991

[54] STRAWBERRY PLANT NAMED 'E26'

[75] Inventors: Harold A. Johnson, Jr.; Thomas M. Sjulin; Amado Q. Amorao; Joseph I. Espejo, Jr., all of Watsonville, Calif.

[73] Assignee: Driscoll Strawberry Associates, Inc., Watsonville, Calif.

[21] Appl. No.: 413,491

[22] Filed: Sep. 27, 1989

[51] Int. Cl.[5] ..... A01H 5/00

[52] U.S. Cl. ..... Plt./49

[58] Field of Search ..... Plt./49

*Primary Examiner*—Howard J. Locker

*Attorney, Agent, or Firm*—Townsend and Townsend

[57] ABSTRACT

A new and distinct everbearing variety of strawberry characterized by its low growing plant that responds to nitrogen fertilizer and cold storage chilling and is considered a high chilling type.

The variety is also distinguished by its ability to initiate a large main crop even late in the fall and winter following a summer planting. The fruit that is produced is of good quality and is easily accessible to pickers.

1 Drawing Sheet

DESCRIPTION

This invention relates to a new and distinct everbearing variety of strawberry known as 'E26', which is the result of a cross of a patented Driscoll Strawberry Associates, Inc. variety 'E23', U.S. Plant Pat. No. 4,763, an ever-bearing variety and a non-patented selection D5.23, recognized as a short day or spring variety.

The seedlings resulting from the aforementioned cross were grown and asexually multipled by runners in Shasta County, Calif., and tested in the fruiting beds on the property of growers of the Driscoll Strawberry Associates, Inc. Clones of the seedlings were also held at the propagation nursery in Shasta County. One plant was selected from the aforementioned group of seedlings and further asexually reproduced in the Shasta County nursery of Driscoll Strawberry Associates, Inc. Tests followed in various parts of California during intervening seasons on various properties of grower members of the Driscoll Strawberry Associates, Inc. These tests indicated the merits of 'E26' and resulted in its selection as a promising test variety.

In the drawing, FIG. 1 is a photograph of plant parts of the new variety, typical in size, shape and color.

The berry in cross section illustrates flesh color, and characteristic core cavity. The inflorescence pictured illustrates typical branching and relative size in October in Oxnard, Calif. The inflorescence pictured shows only two secondary peduncles, but three may be present. Six to eight berries may be produced per inflorence as the photograph shows. Near the ripe primary, which usually doesn't extend past secondary or tertiary berries, are the fused pedicels of a tertiary berry and a quaternary flower. A leaf is present showing a short petiole which is typical. Bracts are sometimes present on the petiole and, when they are present, they develop on the petiole close to the leaflets which is distinct. The crown crop flowers produced after the transplants are planted come rapidly, especially when planted in June or July in Southern California. Ripe fruit may mature within 5 weeks of planting, and 28 days from bloom. It is common practice to de-blossom these crown crop flowers and it is often done within 21 days of a July 1st planting date. Primary flowers are present showing anthers with abundant pollen and a calyx with a double row of sepals with only a few serrations present which is typical. The ripe primary is typical in form and shape, with some concave recesses present giving the berry an irregular conic but glossy appearance. During the late spring and summer, these irregularities may or may not be present, but the primaries, as well as secondaries, may be smooth as well as symmetrically conic. The seed in this illustration is held slightly inserted to equal to the fruit surface, but may also be exerted.

The novel plant of 'E26' is usually small to medium in size, even when given two to three months cold storage after being dug after receiving adequate chilling at the nursery. It does respond to nitrogen fertilizer by becoming more vigorous to help support the large crop that is normally initiated.

The fruit of 'E26' is consistently larger in size but not as smooth a fruit surface as its parent 'E23'. When summer planted after cold storage, 'E26' continues production after its crown crop, whereas, 'D5.23', its other parent, produces a crown crop and then vegetates. Comparing yield, when planted July 8, 'E26' produced in the Fall (September through December) 2,000 to 2,500 crates per acre at Oxnard, which is somewhat superior to 'E23' but is significantly greater than the 300 to 400 crates per acre produced by 'D5.23'.

The physical characteristics of 'E26' are best compared with its related varieties 'Swede', U.S. Plant Pat. No. 6,191, and 'Mr. P', U.S. Plant Pat. No. 5,840. The fruit produced by this new variety is capable of good size, but not as large as those of 'Swede', or the everbearing variety 'Mr. P'. 'E26' will mature more quaternary fruit than the variety 'Swede', and thus influence the average fruit size of 'E26' as compared to 'Swede'.

It also differs from 'Swede' in that its petioles are shorter and not as thick, and its leaflets are smaller. The leaflets are not as dark as 'Swede.' If bracts are present on 'E26,' they develop closer to the leaflets than 'Swede' or 'Mr. P.' The plant is not as vigorous as 'Swede.' The inflorescence length of the new variety is shorter than that of 'Swede' or 'Mr. P' and individual peduncles and petioles are not as thick. The hair on pedicels is not as conspicuous on the new variety and the hair on pedicles holding tertiary berries is held irregularly parallel to an angle of 45 degrees on the tertiary in contrast to the 90 degrees angle of 'Swede' and 'Mr. P.' The pedicel length of the new variety is shorter than that of 'Swede' and 'Mr. P.'

The fruit of 'E26' doesn't become as dark as 'Swede,' but tends to vary in shape and outline in contrast to 'Swede.' 'Swede' is generally smoother than the new variety even though its main crop primaries may split at the apex more often than 'E26.' 'E26,' however, is prone to produce folded seedy tips on its primiaries at times, especially on berries that are short wedge in outline. 'E26' has not rated as favorably as 'Swede' in holding tests done during the summer in Watsonville, and 'E26' is prone to show picking bruises that darken in storage. 'E26' fruit firmness in October and November in Oxnard however, has been quite acceptable and has shown satisfactory ratings in fruit arrival at the marketplace. The calyx of the new variety isn't as large as that of 'Swede,' but is more prone to be held in a reflexed position in contrast to 'Swede.' Individual sepals are similar with serrations not abundant on primaries of both varieties. The isozymes of a leaf extract of the new variety are different in that the phosphoglucoisomerase (PGI) is A2 vs. A1 on 'Swede.'

'E26' has the ability to continue to produce during the late fall and winter when planted during the summer. This is in contrast to 'Swede' and even other everbearers such as 'E24,' Driscoll U.S. Plant Pat. No. 4,988, which doesn't initiate as many flowers during a short day length. 'E26' can be grown at either high or low elevations in California nurseries, and favorable plant production in cold storage has been realized from plants dug in November from high elevation, and planted in July.

'E26' is susceptible to Verticillium wilt, powdery mildew and anthracnose disease caused by *Colletotrichum acutatum.* It has shown some field tolerance to Mycosphaerella leaf spot as well as angular leaf spot. The plant is susceptible to injury from two-spotted spider mite as well as flower thrip.

Flavor panelists have given the fruit from this variety high ratings, but not as high as 'Swede.'

The varietal characteristics of the novel plant described below in detail were observed in Watsonville during July and in Oxnard during October. Both locations are near the Pacific Ocean. The measurements were made from plants planted in January in Watsonville and July in Oxnard and the plants had been dug at a high elevation nursery during November in Shasta County, Calif.

The color terminology is in accordance with the Munsell color system.

Plant — Small to medium and produces a multiple crown. Chilling from cold storage strengthens its plant vigor and this variety is considered a high chilling variety.

Leaves — Mostly medium in size, petioles of vigorously growing plants 10 to 15 cm in length and width of central leaflets is usually 6 to 8 cm. When bracts on petioles are present, they are mostly 10 to 15 cm from leaflets. Leaflets are moderately rugose with serrations that are also moderately deep and ovate, but short acute at the apex, not sharply acute at the apex. Color of leaflets is 1.5G 2.8/7.4 to 9.3Y 3.0/6.8.

Isozymes in leaf extract: Phosphoglucoisomerase (PGI) 3-banded [1]A2. Leucine aminopepghase (LAP) 2-banded A4. Phosphoglucomutase (PGM) 2-banded A1.

[1]As designated by R. Bringhurst. This testing was done by Driscoll Strawberry Associates Laboratory following the procedure described in publication: "Electrophoretic Characterization of California Strawberry Cultivars' by Bringhurst — 1981.

Runners — Vigorous and abundant for an everbearer, both at the nursery and in the fruiting bed, especially when planted in the summer after a long period of cold storage.

Inflorescence — Mostly short in total length, but some may reach 25 cm in length. The common peduncle is mostly short, but may reach 10 cm in length. There are mostly two secondary peduncles, but three are not uncommon. The diameter of pedicels holding primary fruit is moderate in diameter, usually not over 2 mm, and the length of pedicels is not considered long. The pedicel holding the primary berry usually originates at the axial of secondary peduncels, but may originate from a secondary peduncle. The hair on the pedicel of secondary or tertiary fruit is held irregularly parallel to an angle of 45 degrees with the pedicel. One inflorescence may produce 6 to 8 berries with some quaternary flowers maturing fruit. Flowers may be visible above the plant and individual flowers are considered moderate in size and produce an abundance of pollen on their anthers. Pedicels of quaternary berries may be fused to pedicels holding tertiary berries.

Fruit — Berries of the primary crop are not as large as primaries of the main crop in Watsonvill during July. Primaries of the main crop in Watsonville during July are mainly 35 to 45 mm in length with the width averaging 4 mm than the length. Considerable variation in fruit shape. Primaries vary from short wedge to conic as pictured in USDA Bulletin 1043. The wedge shaped fruit may become seedy at the apex at times and the conic fruit varies from smooth symmetrical to non-symmetrical but conic in outline with the concave areas near the apex being common. The shoulders of the fruit are rounded and may cause the calyx to be reflexed. The fruit surface has a good gloss. The color of the fruit surface is 6.0R 3.1/12.0 to 5.5R 2.4/8.5 and the flesh varies from 5.1R 4.1/16.1 to white near the core. The core and core cavity is medium in size. The shelf life is considered good. The medium sized seed that darken in full light can become sunken at times. The seed are prone to become phylloid and show foleaceous growth during the winter and spring production following the first producing year.

Calyx — Primary fruit is medium to large in dimater with a double row of sepals that generally overlap each other. Individual sepals are elliptical to ovate in outline and most of them are not serrated. The calyx is usually clasping to the fruit, but can be reflexed. The color of sepals facing fruit is 8.1GY 3.7/76 and individual sepals may be lighter in color near the fruit.

We claim:

1. The new and distinct variety of strawberry plant herein described and illustrated, and identified by the characteristics enumerated above.

* * * * *

UNITED STATES PATENT AND TRADEMARK OFFICE

CERTIFICATE OF CORRECTION

PATENT NO. : Plant 7,522

DATED : May 14, 1991

INVENTOR(S) : Johnson, Jr. et al.

It is certified that error appears in the above-identified patent and that said Letters Patent is hereby corrected as shown below:

Column 4, line 1, delete "A4" and substitute --B3--;
line 2, delete "A1" and substitute --C2--.

Signed and Sealed this

Fifth Day of October, 1993

*Attest:*

Bruce Lehman

BRUCE LEHMAN

*Attesting Officer*

*Commissioner of Patents and Trademarks*